US005739409A

United States Patent [19]
Fischer et al.

[11] Patent Number: 5,739,409
[45] Date of Patent: *Apr. 14, 1998

[54] ENDOGENOUSLY SWEETENED TRANSGENIC PLANT PRODUCTS

[75] Inventors: Robert Fischer, El Cerrito; Sung-Hou Kim; Joong Myung Cho, both of Moraga; Lola Penarrubia, Berkeley; James Giovannoni, San Francisco; Rosalind Kim, Moraga, all of Calif.

[73] Assignees: The Regents of the University of California, Oakland; Lucky Biotech Corp., Emeryville, both of Calif.

[*] Notice: The term of this patent shall not extend beyond the expiration date of Pat. No. 5,234,834.

[21] Appl. No.: 483,415

[22] Filed: Jun. 7, 1995

Related U.S. Application Data

[62] Division of Ser. No. 962,881, Oct. 19, 1992, which is a continuation of Ser. No. 557,222, Jul. 24, 1990, Pat. No. 5,234,834, which is a continuation-in-part of Ser. No. 465,585, Jan. 18, 1990, abandoned, and Ser. No. 502,257, Mar. 30, 1990, Pat. No. 5,264,558, which is a continuation-in-part of Ser. No. 64,341, Jun. 19, 1987, abandoned, Ser. No. 64,343, Jun. 19, 1987, abandoned, and Ser. No. 117,124, Nov. 4, 1987, abandoned.

[51] Int. Cl.$^6$ .............................. A01H 4/00; C12N 15/82; C12N 5/14
[52] U.S. Cl. ................................ 800/205; 800/DIG. 13; 800/DIG. 44; 800/250; 435/320.1; 435/419; 47/58
[58] Field of Search ............................ 800/205, 250, 800/DIG. 13, DIG. 44; 435/320.1, 172.3, 69.1, 240.4, 419; 536/23.6; 47/58

[56] References Cited

U.S. PATENT DOCUMENTS 3,998,798  12/1976  Cagan et al. ............................ 530/350

FOREIGN PATENT DOCUMENTS 8810265  12/1988  WIPO.
8810271  12/1988  WIPO.
8810303  12/1988  WIPO.

OTHER PUBLICATIONS

Alberts et al., "The Molecular Bilogy of the Cell," (1989), Second Edition, M. Robertson ed., Garland Publishing, Inc., New York, pp. 261–262.

Aleksandrova et al. *Sadovodstvo* (1986) 6(2):27–28.
Bohak et al., *Biochim Biophys Acta* (1976) 427:153–170.
Burpee Catalog 1986, pp. 116, 136, 134, 129, 122, 126, 139, 173.
Cagan, *Science* (1973) 181:32–35.
Christoffersen et al., *Plant Molecular Biol* (1984) 3:385–391.
Deikman et al., *EMBO J* (1988) 7(11):3315–3320.
De Vos et al., *Proc. Natl Acad Sci USA* (1985) 82:1406–1409.
Edens et al., *Gene* (1982) 18:1–12.
Edens et al., *Cell* (1984) 37:629–633.
Frank et al., *Z Physiol Chem* (1976) 357:585–592.
Giovannoni et al., *The Plant Cell* (1989) 1:53–63.
Gordon-Kamm et al., *The Plant Cell* (1990) 2:603–618.
Higginbotham, "Developments in Sweeteners–1," Hough et al., eds., *Applied Science Publications*, London (1979) Chapter 4, pp. 87–123.
Hudson et al., *Biochem Biophys Res Comm* (1976) 71(1):212–220.
Inglete, *Food Technology* (1981) 35(3):34–41.
Kim et al., *Trends in Biochemical Sciences* (1988) 13:13–15.
Kim et al., *Protein Engineering* (1989) 2:571–575.
Lee et al., *Biochemistry* (1988) 27:5101–5107.
Lincoln et al., *Proc. Natl Acad Sci USA* (1984) 84:2793–2797.
Michaels et al. *Crop Science* (1986) 26:104–107.
Morris et al., *Biochim Biophys Acta* (1972) 261:114–122.
Morris et al., *J Biol Chem* (1973) 248(2):534–539.
Ogata et al., *Nature* (1987) 328:739–742.
Potrykus *Bio/Technology* (1990) 8:535–542.
Van der Wel et al., *FEBS Lett* (1973) 29(2):181–184.

*Primary Examiner*—Che S. Chereskin
*Attorney, Agent, or Firm*—Morrison and Foerster LLP

[57] ABSTRACT

Edible fruit, seed and vegetables of transgenic plants modified to produce a sweetening protein such as monellin or thaumatin are useful in preparing food compositions which have enhanced sweetness improved flavor. Expression systems for the genes encoding sweetening proteins compatible with plant systems and designed to enhance the production of these proteins in the edible portions of plants, and methods for producing sweetened fruit, seeds and vegetables are described.

32 Claims, 4 Drawing Sheets

AMINO ACID SEQUENCE OF NATURAL MONELLIN

A-Chain

1
```
*PHE ARG GLU ILE  LYS GLY TYR GLU TYR GLN
 LEU TYR VAL TYR  ALA SER ASP LYS LEU PHE
 ARG ALA ASP ILE  SER GLU ASP TYR LYS THR
 ARG GLY ARG LYS  LEU LEU ARG PHE ASN GLY
 PRO VAL PRO PRO  PRO
                   45
```

B-Chain

1
```
 GLY GLU TRP GLU ILE  ILE ASP ILE  GLY PRO
 PHE THR GLN ASN LEU  GLY LYS PHE ALA VAL
 ASP GLU GLU ASN LYS  ILE  GLY GLN TYR GLY
 ARG LEU THR PHE ASN  LYS VAL ILE  ARG PRO
 CYS MET LYS LYS THR  ILE  TYR GLU ASN GLU
                                         50
```

*PHE present only in 10% of natural monellin

FIG. 1

```
ATG GGA GAA TGG GAA ATT ATC GAT ATT GGA CCA TTC ACT CAA AAC TTG GGT AAG TTC GCT GTT GAC GAA GAA AAC AAG ATT GGT CAA TAT
Met Gly Glu Trp Glu Ile Ile Asp Ile Gly Pro Phe Thr Gln Asn Leu Gly Lys Phe Ala Val Asp Glu Glu Asn Lys Ile Gly Gln Tyr
                              30                              60                              90

|———————B———————>
GGT AGA TTG ACT TTC AAC AAG GTT ATT AGA CCA TGT ATG AAG ACT ATT TAC GAA AAC GAA AGA GAA ATT AAG GGG TAC GAA TAC CAA
Gly Arg Leu Thr Phe Asn Lys Val Ile Arg Pro Cys Met Lys Thr Ile Tyr Glu Asn Glu Arg Glu Ile Lys Gly Tyr Glu Tyr Gln
                              120                             150                             180

TTG TAT TAC GCT TCT GAC AAG CTT TTC AGA GCT GAC TAC AAG TCT GAA GAC TAC AAG ACC CGC GGT AGA AAG TTG AGA TTC AAC GGT
Leu Tyr Tyr Ala Ser Asp Lys Leu Phe Arg Ala Asp Tyr Lys Ser Glu Asp Tyr Lys Thr Arg Gly Arg Lys Leu Arg Phe Asn Gly
                              210                             240                             270
                                                                        <———————A———————|

CCA GTT CCA CCA CCA
Pro Val Pro Pro Pro
```

FIG. 3

FUSED MONELLIN I

5'
NcoI                    ClaI

```
C ATGGGAGAAT GGGAAATTAT CGATATTGGA CCATTCACTC AAAACTTGGG
   CCTCTTA   CCCTTTAATA GCTATAACCT GGTAAGTGAG TTTTGAACCC

TAAGTTCGCT GTTGACGAAG AAAACAAGAT TGGTCAATAT GGTAGATTGA
ATTCAAGCGA CAACTGCTTC TTTT GTTC TA ACCAGTTATA CCATCTAACT

CTTTCAACAA GGTTATTAGA CCATGTATGA AGAAGACTAT TTACGAAAAC
GAAAGTTGTT CCAATAATCT GGTACATACT TCTTCTGATA AATGCTTTTG

GAAAGAGAAA TTAAGGGGTA CGAATACCAA TTGTATGTTT ACGCTTCTGA
CTTT CTC TTT AATTCCCCAT GCTTATGGTT AACATACAAA TGCGAAGACT

CAAGCTTTTC AGAGCTGACA TTTCTGAAGA CTACAAGACC CGCGGTAGAA
GTTCGAAAAG TCTCGACTGT AAAGACTTCT GATGTTCTGG GCGCCATCTT

AGTTGTTGAG ATTCAACGGT CCAGTTCCAC CACCATAATA G
TCAACAACTC TAAGTTGCCA GGTCAAGGTG GTGGTATTAT CAGCT
                                        SalI  3'
```

FIG. 4

ENDOGENOUSLY SWEETENED TRANSGENIC PLANT PRODUCTS

This application is a division of application Ser. No. 07/962,881 filed 19 Oct. 1992, which is a continuation of application Ser. No. 07/557,222 filed 24 Jul. 1990, now U.S. Pat. No. 5,234,834, which is a continuation-in-part of U.S. Ser. No. 07/502,257 filed 30 Mar. 1990, now U.S. Pat. No. 5,264,558 which is a continuation-in-part of U.S. Ser. Nos. 064,341 and 064,343, both filed 19 Jun. 1987, both now abandoned and of U.S. Ser. No. 117,124 filed 4 Nov. 1987, now abandoned and its continuation application U.S. Ser. No. 465,585 filed 18 Jan. 1990.

GOVERNMENT SUPPORT

This invention was made with Government support under Grant Nos. GM33856 and NS15174 awarded by the National Institute of Health and Grant No. CRCR-87-1-2526 awarded by the U.S. Department of Agriculture. The Government has certain rights in this invention.

TECHNICAL FIELD

The invention relates to recombinant manipulation of plants which are useful in food production. More specifically, it concerns fruits, vegetables and seeds with enhanced sweetness and flavor produced by transgenic plants which exhibit controlled expression of genes encoding sweet-tasting proteins, including the monellin and thaumatin genes.

BACKGROUND OF THE INVENTION

It is well known that certain proteinaceous compounds have the ability to substitute in a highly effective manner for sugar in giving foods and beverages a sweet taste. The simplest of these examples is aspartame, which is a dipeptide derivative and currently on the market. However, two much more complex proteins, monellin and thaumatin have been isolated from plant sources.

Thaumatin is isolated from *Thaumatococcus daniellii*, a West African plant having triangular shaped fruit at ground level. The natural protein product, thaumatin, has an average sweetness of 2500 times that of sucrose and has been marketed under the trademark Talin. The three-dimensional structure of this protein has been studied and the results published by De Vos, A. M., et al., *Proc Natl Acad Sci* USA (1985) 82: 1406–1409. At least five highly related forms of thaumatin (I, II, III, b and c) have been identified (Higginbotham, J. D. in *Developments in Sweeteners-1* (Hough, C. A. M. et al., eds.) Applied Science Publications, London 1979, pp. 87–123. Furthermore, the gene encoding the Thaumatin II protein has been cloned and its sequence has been determined by Edens, L., et al., *Gene* (1982) 18: 1. Thaumatin has also been produced recombinantly in bacteria (Edens, L., et al., *Gene* (1982) 18: 1) and yeast (Edens, L., et al., *Cell* (1984) 37: 629); Lee, et al, *Biochemistry* (1988) 27: 5101).

The other protein is isolated from "Serendipity Berries" of the West African Plant *Dioscoreophyllum comminisii*. The amino acid sequence of monellin is known, and the three-dimensional structure of this protein has been determined by Ogata, C., et al., *Nature* (1987) 328: 739–742. Monellin has been characterized by Morris et al., *J Biol Chem* (1973) 248: 534–539, and by others; Cagan, *Science* (1973) 181: 32–35; Bohak and Li, *Biochim Biophys Acta* (1976) 427: 153–170; Hudson and Beeman, *Biochem Biophys Res Comm* (1976) 71: 212–220; Van der Wel and Loeve, *FEBS Lett* (1973) 29: 181–183; Frank and Zuber Hoppe-Seyler's *Z Physiol Chem* (1976) 357: 585–592; Morris and Cagan, *Biochim Biophys Acta* (1972) 261: 114–122. U.S. Pat. No. 3,998,798 describes the preparation of natural monellin.

The known amino acid sequence of the A and B chains of natural monellin is shown in FIG. 1. It is a two chain protein, one "A" chain containing 45, and the other "B" chain, 50 amino acid residues. The three-dimensional conformation of the protein, shown in FIG. 2, is evidently essential for its activity because when native monellin is heated to 90° C. at neutral pH or to 50° C. at acidic pH and then cooled, the sweetness is destroyed. The B chain containing 50 amino acids is intimately associated with the A chain of 45 amino acids in such a way that there are many interchain interactions. Heating of the protein, evidently dissociates the chains in such a way that they are incapable of reforming into the appropriate conformation.

The parent applications herein, now published as PCT application WO 88/10265 and European application EP 318,580 and EP 323,489, and Kim, S.-H., et al., *Protein Engineering* (1989) 2: 571–575 describe the apparent stabilization of the conformation by synthesizing appropriate portions of the A and B chains as part of a single protein, and the recombinant production of the single chain form of monellin. Various amino acid sequences can be used to form a linkage between amino acid 46 (Ile) of the B chain with amino acid 6 (Gly) of the A chain. As described in these references, limited modifications of the A and B chain portions of the resulting single chain monellin may also be included. These modifications are made possible by the availability of the gene encoding the single chain sequence, which was synthesized using commercially available methods.

Monellin and thaumatin are the only proteins currently known which have a high specificity for human sweet taste receptors, thus resulting in a highly sweetening effect. Comparison of thaumatin and monellin amino acid sequences shows no significant homology either in amino acid sequence or in their three dimensional backbone structures (Kim, S.-H., et al., *Trends in Biochemical Sciences* (1988) 13: 13). However, it may be that other as yet undiscovered proteins with this property exist and it is quite likely that only a limited region of the three dimensional structure is required for the human taste receptor specificity displayed by these proteins.

It has now been found that in addition to recombinant manufacture of substantial quantities of monellin and of thaumatin using recombinant methods, edible parts of plants can be provided in "naturally" sweetened form by producing these edible materials as fruits, seeds or vegetative parts of transgenic plants wherein the transgenic plants are modified from their natural counterparts by introduction of an expression system for the thaumatin or monellin gene or the single chain monellin gene. The choice of control sequences in the expression system also permits targeting of the expression to the desired plant tissue, and expression at the appropriate time in development.

DISCLOSURE OF THE INVENTION

The invention provides plant derived foodstuffs which are endogenously sweetened and improved in flavor by production of thaumatin or monellin in the development of the plant from which the foodstuffs are derived. Fruits, for example, with enhanced sweet taste can be produced by placing thaumatin or monellin coding sequences under control of promoters which are activated during the ripening process. Seeds can be sweetened by using control systems for seed storage proteins as control systems for thaumatin or monellin. Vegetable portions of plants can be sweetened by introduction of the thaumatin or monellin gene under control of sequences which operate as constitutive promoters, or by using vegetable-specific promoters. Thus, the transformed plants can be modified in controlled ways to provide enhanced sweetness at the desired locations and at the desired state of development.

Accordingly, in one aspect, the invention is directed to expression systems capable of production of single chain monellin, at least one of the two chains of the monellin dimeric protein, or thaumatin in plant tissue. These expression systems comprise the monellin coding sequence or thaumatin coding sequence operably linked to plant-compatible control sequences. Of particular interest are control sequences which are associated with ripening of fruits.

In other aspects, the invention is directed to plant cells transformed with the expression systems described above, to plants regenerated from or containing these cells, to edible portions of these plants, and to foodstuffs prepared from them. In other aspects, the invention is directed to methods to produce fruits, seeds and vegetables with enhanced sweetness which method comprises cultivation of the transgenic plants of the invention followed by recovery of the desired edible portions.

BRIEF DESCRIPTION OF THE DRAWINGS

FIG. 1 (SEQ ID NO:1 and SEQ ID NO:2) shows the amino acid sequence of the A and B chains of native monellin.

FIG. 3 (SEQ ID NO:3 and SEQ ID NO:4) shows a DNA sequence of a fused monellin gene and its corresponding amino acid sequence.

FIG. 4 (SEQ ID NO:5 and SEQ ID NO:6) shows the complete sequence of the synthetic insert containing the coding region shown in FIG. 3.

MODES OF CARRYING OUT THE INVENTION

Figure 2:
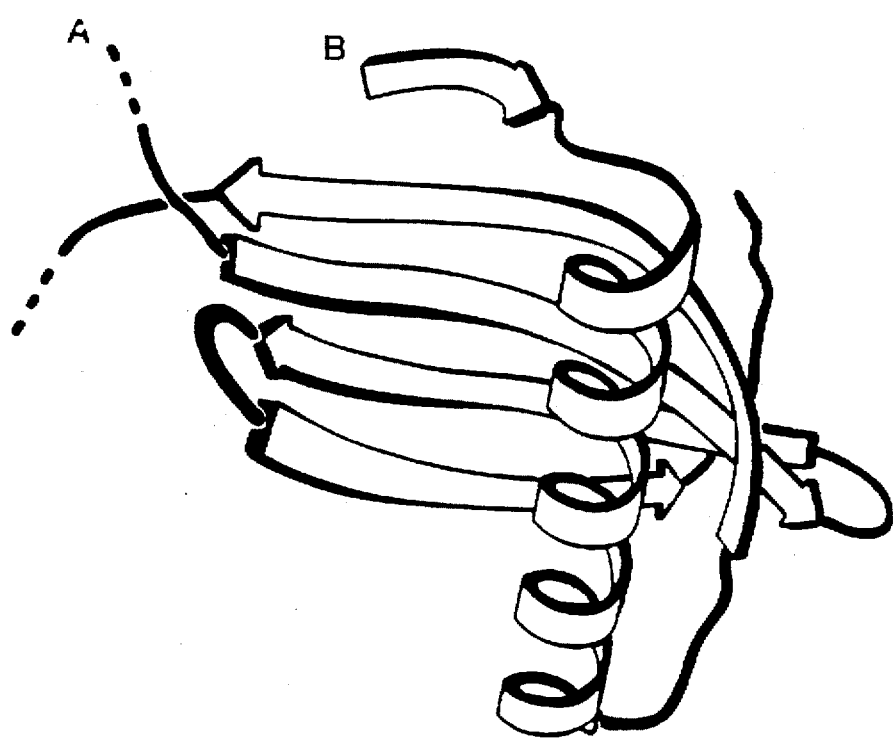
FIG. 2 shows the three-dimensional backbone structure of the native monellin protein.

By "sweetener protein" is meant a protein which imparts a sweetening power at least 50 times that of sucrose. Although this is the primary mode of action, it is understood that the overall flavor of the edible plant portion will be generally improved. Thus, when "enhanced sweetness" is referred to, it is understood that noticeable effects on flavor to alter it in what may be perceived as additional ways is also indicated. Although monellin and thaumatin are the only sweetener proteins presently known, others may also exist and could be employed similarly.

As used herein, the term "monellin" refers to single chain monellin or fused monellin, as defined below, as well as to the dimeric protein substantially as depicted in FIGS. 1 and 2. It is often convenient to use "single chain monellin" or "fused monellin" which has the formula B-C-A and consists essentially of a peptide portion (B) substantially equivalent to the sequence of residues 1–46 of the B chain (which corresponds to Subunit II of native monellin) linked through the C-terminus either directly by a covalent bond or using a covalent linker comprising a peptide residue of 1–10 amino acid residues (C) to the N-terminus of a peptide (A) substantially equivalent to the sequence of residues 6–45 of A chain corresponding to Subunit I of native monellin. By "substantially equivalent" is meant a peptide which, in the context of the compounds of the invention, results in a substance having a sweetening power at least 50 times that of sucrose, and which has at least 30%–50% homology with the peptide represented by residues 1–46 of the B chain or to the peptide represented by residues 6–45 of the A chain, preferably 80% homology. At least 90% homology is preferred, especially including conservative substitutions.

Similar statements apply to the definition of "thaumatin" as used herein. As set forth in the Background section above, the DNA encoding thaumatin II and its deduced amino acid sequence are known; other forms of thaumatin are generally homologous with thaumatin II. The thaumatin useful in the invention is "substantially equivalent" to these naturally occurring forms of thaumatin, and wherein "substantially equivalent" means that the peptide is a substance having a sweetening power at least 50 times that of sucrose and at least 30%–50% homology with at least one form of the native thaumatin protein, preferably 80% homology and most preferably 90% homology especially including conservative substitutions.

Homology is calculated by standard methods which involve aligning two sequences to be compared so that maximum matching occurs, and calculating the percentage of matches. Thus, in one particularly preferred embodiment, the substances of the invention comprise a peptide having the amino acid sequence of residues 1–46 of the native monellin B chain linked (through the linker) to a peptide having the primary structure represented by residues 6–45 of the native monellin A chain. Substantially equivalent substances to these include those wherein one or more of the residues of the native sequence is deleted, substituted for, or inserted by a different amino acid or acids.

Preferred substitutions are those which are conservative, i.e., wherein a residue is replaced by another of the same general type. As is well understood, naturally occurring amino acids can be subclassified as acidic, basic, neutral and polar, .or neutral and nonpolar. Furthermore, three of the encoded amino acids are aromatic. It is generally preferred that peptides differing from the native sequence contain substitutions which are from the same group as that of the amino acid replaced. Thus, in general, the basic amino acids Lys and Arg are interchangeable; the acidic amino acids aspartic and glutamic are interchangeable; the neutral polar amino acids Ser, Thr, Cys, Gln, and Asn are interchangeable; the nonpolar aliphatic acids Gly, Ala, Val, Ile, and Leu are conservative with respect to each other (but because of size, Gly and Ala are more closely related and Val, Ile and Leu are more closely related), and the aromatic amino acids Phe, Trp, and Tyr are interchangeable. While proline is a nonpolar neutral amino acid, it represents difficulties because of its effects on conformation, and substitutions by or for proline are not preferred, except when the same or similar conformational results can be obtained. Polar amino acids which represent conservative changes include Ser, Thr, Gln, Asn; and to a lesser extent, Met. In addition, although classified in different categories, Ala, Gly, and Ser seem to be interchangeable, and Cys additionally fits into this group, or may be classified with the polar neutral amino acids. Some substitutions by amino acids from different classes may also be useful to modify sweet taste responses.

In general, whatever substitutions are made are such that the sweetness of the intact proteinaceous molecule is retained and ancillary properties, such as non-toxicity are not substantially disturbed.

It should be further noted that if the protein embodiments of the invention are produced recombinantly as intracellular proteins, an N-terminal methionine residue may be retained in the finished product. Cleavage of this N-terminal methionine to liberate the native sequence may or may not be complete. In addition, the sweetening peptide or protein may be produced as a fusion protein with additional heterologous upstream or downstream sequence.

With respect to the monellin embodiment, the nature of the designation "C" in the B-C-A monellin formula refers to either simply a covalent bond or to a peptide residue of 1–10 amino acids. One preferred covalent peptide linking sequence is Tyr-Glu-Asn-Glu-Arg-Glu-Ile-Lys                (SEQ ID NO:7), which corresponds to the amino acids in positions 47–50 of the monellin B chain (Subunit II) followed by the amino acids in positions 2–5 of the A chain (Subunit I). The amino acid Phe, in position 1 of the A chain, is absent from the major species of native protein.

The peptide represented by C contains at least 30%–50%, preferably at least about 75% of polar amino acids. Also preferably, at least about 25% and more preferably about 50% are amino acids naturally occurring at the relevant termini of the subunits.

A particularly preferred group of peptide represented by C contains 3–10, preferably 6–8, amino acid residues and is of the formula

A1-A2-A3-A4-A5-A6-A7-A8-A9-A10 wherein each A1–A10 may be an amino acid residue or may be absent, but at least three of A1–A10 must be amino acid residues. In a particularly preferred group of embodiments, A9 and A10 are absent, A2, A4 and A6 are acidic amino acids; A5 and A8 are basic amino acids, A3 is a polar/neutral amino acid, and A1 and A7 are nonpolar amino acids.

In another set of preferred embodiments, A9 and A10 are absent, and

A1 is Ala, Asp, Glu, Lys, Arg or Tyr;

A2 is Tyr, Ala, Asp, Glu, Asn, Gln, Arg, Thr, or Ser;

A3 is Asn, Gln, Ser, Thr, Asp, Gly, Arg or Tyr;

A4 is Phe, Trp, Tyr, Ser, Thr, Asp, Lys or Arg;

A5 is Asp, Glu, Lys, Arg, Leu or Thr;

A6 is Asp, Glu, Val, Ile, Leu, Lys or Arg;

A7 is Gly, Ala, Val, Ile, Leu, Lys or Arg; and

A8 is Lys or Arg;

wherein at least 75% of these amino acids are polar and wherein one or more of A1–A8 may be absent. In another set of preferred embodiments, A9 and A10 are absent and the remaining amino acids are present in embodiments according to:

A1 is Tyr or Glu;

A2 is Asp, Glu, Tyr or Lys;

A3 is Asn, Thr, Ala or Tyr;

A4 is Arg, Ser, Lys or Glu;

A5 is Glu, Asp or Thr;

A6 is Lys, Asp or Arg;

A7 is Gly, Ile or Leu; and

A8 is Lys or Arg;

wherein at least 75% of the residues are polar and one or more of A1–A8 may be absent.

In a particularly preferred set of embodiments, A9 and A10 are absent, A1 is Tyr or Phe, A2 is Glu or Asp, A3 is Asn or Gln, A4 is Glu or Asp, A5 is Arg, His, or Lys, A6 is Glu or Asp, A7 is Ile, Val, or Leu, and A8 is Arg, Lys, or His.

Particularly preferred are the following bridges:

Tyr—Glu—Asn—Arg—Glu—Asp—Ile—Lys (SEQ ID NO:8);
Tyr—Lys—Thr—Arg—Glu—Asp—Ile—Lys (SEQ ID NO:9);
Tyr—Glu—Arg—Glu—Ile—Lys (SEQ ID NO:10);
Tyr—Glu—Asn—Ile—Lys (SEQ ID NO:11);
Tyr—Glu—Ile—Lys (SEQ ID NO:12);
Tyr—Tyr—Ala—Ser—Asp—Lys—Leu—Lys (SEQ ID NO:13);
Tyr—Ala—Ser—Asp—Lys (SEQ ID NO:14);
Tyr—Ala—Ser—Asp—Lys—Leu (SEQ ID NO:15);
Tyr—Ser—Asp—Lys (SEQ ID NO:16);
Glu—Asp—Tyr—Lys—Thr—Arg—Gly—Arg (SEQ ID NO:17); and
Glu—Asp—Tyr—Thr—Arg (SEQ ID NO:18).

Usually there will be at least one Tyr, Glu, Asp, Lys or Arg present in the chain, and more usually at least one of Glu, Asp, Lys or Arg. Preferred amino acids for the bridge are Tyr, Ile, Ser, Thr, Asp, Glu, Lys, Arg, Asn and Gln where more than 50% of the amino acids of the bridge will be selected from this group.

According to the invention herein, rather than providing the sweetener proteins as independent products, the coding sequences for monellin or thaumatin can be inserted into specialized expression control DNA sequences which are compatible with higher plants used to obtain transgenic plants to result in naturally sweetened plant products. (If monellin is to be provided in the dimeric form, expression systems for both chains should be transformed into the plant. The system for each chain may be placed on a separate vector, or the two systems may be supplied on a single vector.) Although the primary effect is that of sweetening, it is understood that this can affect the overall flavor and cause general improvement in taste. In these embodiments, control regions which are functional either constitutively or in specialized tissues in plants are employed. Transcription initiation regions, for example, include the various opine initiation regions, such as octopine, mannopine, nopaline and the like. Plant viral promoters can also be used, such as the cauliflower mosaic virus 35S promoter. In addition, plant promoters such as ribulose-1,3-diphosphate carboxylase, fruit-specific promoters, heat shock promoters, seed-specific promoters, etc. can also be used. Plants transformed with this expression system offer production of naturally sweetened fruits, vegetables, and seeds.

A large number of suitable control systems are available. For example, the cauliflower mosaic virus (CaMV) 35S promoter has been shown to be highly active in many plant organs and during many stages of development when integrated into the genome of transgenic plants including tobacco and petunia, and has been shown to confer expression in protoplasts of both dicots and monocots.

The CaMV 35S promoter has been demonstrated to be active in at least the following monocot and dicot plants with edible parts:

blackberry, Rubus; blackberry/raspberry hybrid, Rubus, and red raspberry (Graham et al., *Plant Cell, Tissue and Organ Culture* (1990) 20: 35);

carrot, *Daucus carota* (Thomas et al., *Plant Cell Reports* (1989) 8: 354, Wurtele and Bulka, *Plant Science* (198) 61: 253);

maize (Rhodes et al., *Science* (1988) 240: 204);

potato, Solanum tuberosum (Ishida et al., *Plant Cell Reports* (1989) 8: 325);

rice, *Oryza sativa* (Shimamoto et al., *Nature* (1989) 338: 274);

strawberry, *Fragaria×ananassa* (Nehra et al., *Plant Cell Reports* (1990) 9: 10);

tomato, *Lycopersicon esculentum* (Sheehy et al., *Proc Nat Acad Sci* USA (1988) 85: 8805; Smith et al., *Nature* (1988) 334: 724).

The nopaline synthase (Nos) promoter has been shown to be active in at least the following monocot and dicot plants with edible parts:

apple, *Malus pumila* (James et al., *Plant Cell Reports* (1989) 7: 658);

cauliflower, *Brassica oleracea* (Srivastava et al., *Plant Cell Reports* (1988) 7: 504);

celery, *Apium graveolens* (Catlin et al., *Plant Cell Reports* (1988) 7: 100);

cucumber, *Cucumis sativus* (Trulson et al., *Theor Appl Genet* (1986) 73: 11);

eggplant, *Solanum melongena* (Guri and Sink, *J Plant Physiol* (1988) 133: 52);

lettuce, *Lactuca sativa* (Michelmore et al., *Plant Cell Reports* (1987) 6: 439);

potato, *Solanum tuberosum* (Ishida et al., *Plant Cell Reports* (1989) 8: 325);

rye, *Secale cereale* (de la Pena et al., *Nature* (1987) 325: 274);

strawberry, *Fragaria×ananassa* (Nehra et al., *Plant Cell Reports* (1990) 9: 10);

tomato, *Lycopersicon esculentum* (McCormick et al., *Plant Cell Reports* (1986) 5: 81);

walnut, *Juglans regia* (McGranahan et al., *Plant Cell Reports* (1990) 8: 512).

Organ-specific promoters are also well known. For example, the E8 promoter is only transcriptionally activated during tomato fruit ripening, and can be used to target gene expression in ripening tomato fruit (Deikman and Fischer, *EMBO J* (1988) 7: 3315; Giovannoni et al., *The Plant Cell* (1989) 1: 53). The activity of the E8 promoter is not limited to tomato fruit, but is thought to be compatible with any system wherein ethylene activates biological processes.

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, Phil, *Trans R Soc London* (1986) B314: 343.

These mRNAs are first isolated to obtain suitable probes for retrieval of the appropriate genomic sequence which retains the presence of the natively associated control sequences. An example of the use of techniques to obtain the cDNA associated with mRNA specific to avocado fruit is found in Christoffersen et al., *Plant Molecular Biology* (1984) 3: 385. Briefly, mRNA was isolated from ripening avocado fruit and used to make a cDNA library. Clones in the library were identified that hybridized with labeled RNA isolated from ripening avocado fruit, but that did not hybridize with labeled RNAs isolated from unripe avocado fruit. Many of these clones represent mRNAs encoded by genes that are transcriptionally activated at the onset of avocado fruit ripening.

A somewhat more sophisticated procedure was described in *Molecular Biology of the Cell*, Second Edition (1989) pages 261–262, edited by Alberts et al., Garland Publishing Incorporated, New York. In this procedure, mRNAs enriched for organ-specific nucleic acid sequences were used to construct the cDNA library. This method was also applied to tomato by Lincoln et al., *Proc Natl Acad Sci* (1987) 84: 2793, and resulted in the production of the E8 cDNA clone used to isolate the E8 promoter illustrated herein.

The gene that encodes the organ-specific mRNA is then isolated by constructing a library of DNA genomic sequences from the plant. The genome library is screened with the organ-specific cDNA clone, and the sequence is determined. The promoter is then isolated. These procedures are now considered to be routine and are described in detail in Sambrook et al., *Molecular Cloning: A Laboratory Manual*, Second Edition (1989) Cold Spring Harbor Laboratory Press, Cold Spring Harbor.

Either a constitutive promoter (such as the CaMV or Nos promoter illustrated above) or a desired organ-specific promoter (such as the E8 promoter from tomato or alternate specific promoter isolated using organ-specific cDNA as described above) is then ligated to the gene encoding single chain monellin or thaumatin using standard techniques now common in the art. The expression system may be further optimized by employing supplemental elements such as transcription terminators and/or enhancer elements.

Thus, for expression in plants, the recombinant expression cassette will contain in addition to the monellin-encoding sequence, a plant promoter region, a transcription initiation site (if the monellin-encoding sequence to be transcribed lacks one), and a transcription termination sequence. Unique restriction enzyme sites at the 5' and 3' ends of the cassette are typically included to allow for easy insertion into a pre-existing vector.

Sequences controlling eucaryotic gene expression have been extensively studied. Promoter sequence elements include the TATA box consensus sequence (TATAAT), which is usually 20 to 30 base pairs (bp) upstream of the transcription start site. In most instances the TATA box is required for accurate transcription initiation. By convention, the start site is called +1. Sequences extending in the 5' (upstream) direction are given negative numbers and sequences extending in the 3' (downstream) direction are given positive numbers.

In plants, further upstream from the TATA box, at positions −80 to −100, there is typically a promoter element with a series of adenines surrounding the trinucleotide G(or T)NG (Messing, J. et al., in *Genetic Engineering in Plants*, Kosage, Meredith and Hollaender, eds. (1983) pp. 221–227). Other sequences conferring tissue specificity, response to environmental signals, or maximum efficiency of transcription may also be found in the promoter region. Such sequences are often found within 400 bp of the transcription initiation site, but may extend as far as 2000 bp or more.

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

As stated above, any of a number of promoters which direct transcription in plant cells is suitable. The promoter can be either constitutive or inducible. Promoters of bacterial origin include the octopine synthase promoter, the nopaline synthase promoter and other promoters derived from native Ti plasmids (Herrera-Estrella et al., *Nature* (1983) 303: 209–213). Viral promoters include the 35S and 19S RNA promoters of cauliflower mosaic virus (O'Dell et al., *Nature* (1985) 313: 810–812). Plant promoters include the ribulose-1,3-disphosphate carboxylase small subunit promoter and the phaseolin promoter. The promoter sequence from the E8 gene and other genes in which expression is induced by ethylene may also be used. The isolation and sequence of the E8 promoter is described in detail in Deikman and Fischer, *EMBO J* (1988) 2: 3315–3320 which is incorporated herein by reference.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently processed, DNA sequences which direct polyadenylation of the RNA are also commonly added to the vector construct (Alber and Kawasaki, *Mol and Appl Genet,* (1982) 1: 419–434). Polyadenylation is of importance for expression of the thaumatin or monellin-encoding RNA in plant cells. Polyadenylation sequences include, but are not limited to the Agrobacterium octopine synthase signal (Gielen et al., *EMBO J,* (1984) 3: 835–846) or the nopaline synthase signal (Depicker et al., *Mol and Appl Genet,* (1982) 1: 561–573).

The resulting expression system or cassette is ligated into or otherwise constructed to be included in a recombinant vector which is appropriate for higher plant transformation. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range procaryotic origin of replication is included. A selectable marker for bacteria should also be included to allow selection of bacterial cells bearing the desired construct. Suitable procaryotic selectable markers also include resistance to antibiotics such as kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

In addition, vectors can also be constructed that contain in-frame ligations between the sequence encoding the sweetening protein and sequences encoding other molecules of interest resulting in fusion proteins, by techniques well known in the art.

When an appropriate vector is obtained, transgenic plants are prepared which contain the desired expression system. A number of techniques are available for transformation of plants or plant cells. All types of plants are appropriate subjects for "direct" transformation; in general, only dicots can be transformed using Agrobacterium-mediated infection.

In one form of direct transformation, the vector is microinjected directly into plant cells by use of micropipettes to mechanically transfer the recombinant DNA (Crossway, *Mol Gen Genetics* (1985) 202: 179–185). In another form, the genetic material is transferred into the plant cell using polyethylene glycol (Krens, et al., *Nature* (1982) 296: 72–74), or high velocity ballistic penetration by small particles with the nucleic acid either within the matrix of small beads or particles, or on the surface, is used (Klein, et al., *Nature* (1987) 327: 70–73). In still another method protoplasts are fused with other entities which contain the DNA whose introduction is desired. These entities are minicells, cells, lysosomes or other fusible lipid-surfaced bodies (Fraley, et al., *Proc Natl Acad Sci USA* (1982) 79: 1859–1863).

DNA may also be introduced into the plant cells by electroporation (Fromm et al., *Proc Natl Acad Sci USA* (1985) 82: 5824). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

For transformation mediated by bacterial infection, a plant cell is infected with *Agrobacterium tumefaciens* or *A. rhizogenes* previously transformed with the DNA to be introduced. Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (Schell, J., *Science* (1987) 237: 1176–1183). Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid (Hoekema, et al., *Nature* (1983) 303: 179–189). The transferred DNA region can be increased in size by the insertion of heterologous DNA without its ability to be transferred being affected. Thus a modified Ti or Ri plasmid, in which the disease-causing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to "shuttle vectors," (Ruvkum and Ausubel, *Nature* (1981) 298: 85–88), promoters (Lawton et al., *Plant Mol Biol* (1987) 9: 315–324) and structural genes for antibiotic resistance as a selection factor (Fraley et al., *Proc Natl Acad Sci* (1983) 80: 4803–4807).

There are two classes of recombinant Ti and Ri plasmid vector systems now in use. In one class, called "cointegrate," the shuttle vector containing the gene of interest is inserted by genetic recombination into a non-oncogenic Ti plasmid that contains both the cis-acting and trans-acting elements required for plant transformation as, for example, in the pMLJ1 shuttle vector of DeBlock et al., *EMBO J* (1984) 3: 1681–1689 and the non-oncogenic Ti plasmid pGV3850 described by Zambryski et al., *EMBO J* (1983) 2: 2143–2150. In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, *Nucleic Acids Research* (1984) 12: 8711–8721 and the non-oncogenic Ti plasmid PAL4404 described by Hoekma, et al., *Nature* (1983) 303: 179–180. Some of these vectors are commercially available.

There are two common ways to transform plant cells with Agrobacterium: co-cultivation of Agrobacterium with cultured isolated protoplasts, or transformation of intact cells or tissues with Agrobacterium. The first requires an established culture system that allows for culturing protoplasts and subsequent plant regeneration from cultured protoplasts. The second method requires (a) that the intact plant tissues, such as cotyledons, can be transformed by Agrobacterium and (b) that the transformed cells or tissues can be induced to regenerate into whole plants.

Most dicot species can be transformed by Agrobacterium as all species which are a natural plant host for Agrobacterium are transformable in vitro. Monocotyledonous plants, and in particular, cereals, are not natural hosts to Agrobacterium. Attempts to transform them using Agrobacterium have been unsuccessful until recently (Hooykas-Van Slogteren et al., *Nature* (1984) 311: 763–764). However, there is growing evidence now that certain monocots can be transformed by Agrobacterium. Using novel experimental approaches cereal species such as rye (de la Pena et al., *Nature* (1987) 325: 274–276), maize (Rhodes et al., *Science* (1988) 240: 204–207), and rice (Shimamoto et al., *Nature* (1989) 338: 274–276) may now be transformed.

Identification of transformed cells or plants is generally accomplished by including a selectable marker in the transforming vector, or by obtaining evidence of successful bacterial infection.

Plant cells which have been transformed can also be regenerated using known techniques.

Plant regeneration from cultured protoplasts is described in Evans et al., *Handbook of Plant Cell Cultures*, Vol. 1: (MacMillan Publishing Co. New York, 1983); and Vasil I. R. (ed.), *Cell Culture and Somatic Cell Genetics of Plants*, Acad. Press, Orlando, Vol. I, 1984, and Vol. II, 1986). It is known that practically all plants can be regenerated from cultured cells or tissues, including but not limited to, all major species of sugarcane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

A large number of plants have been shown capable of regeneration from transformed individual cells to obtain transgenic whole plants. For example, regeneration has been shown for dicots as follows:

apple, *Malus pumila* (James et al., *Plant Cell Reports* (1989) 7: 658);

blackberry, Rubus, Blackberry/raspberry hybrid, Rubus, red raspberry, Rubus (Graham et al., *Plant Cell, Tissue and Organ Culture* (1990) 20: 35);

carrot, *Daucus carota* (Thomas et al., *Plant Cell Reports* (1989) 8: 354; Wurtele and Bulka, *Plant Science* (1989) 61: 253);

cauliflower, *Brassica oleracea* (Srivastava et al., *Plant Cell Reports* (1988) 7: 504);

celery, *Apium graveolens* (Catlin et al., *Plant Cell Reports* (1988) 7: 100);

cucumber, *Cucumis sativus* (Trulson et al., *Theor Appl Genet* (1986) 73: 11);

eggplant, *Solanum melongena* (Guri and Sink, *J. Plant Physiol* (1988) 133: 52)

lettuce, *Lactuca sativa* (Michelmore et al., *Plant Cell Reports* (1987) 6: 439);

potato, *Solanum tuberosum* (Sheerman and Bevan, *Plant Cell Reports* (1988) 7: 13);

rape, *Brassica napus* (Radke et al., *Theor Appl Genet* (1988) 75: 685; Moloney et al., *Plant Cell Reports* (1989) 8: 238);

soybean (wild), *Glycine canescens* (Rech et al., *Plant Cell Reports* (1989) 8: 33);

strawberry, *Fragaria x ananassa* (Nehra et al., *Plant Cell Reports* (1990) 9: 10;

tomato, *Lycopersicon esculentum* (McCormick et al., *Plant Cell Reports* (1986) 5: 81);

walnut, *Juglans regia* (McGranahan et al., *Plant Cell Reports* (1990) 8: 512);

melon, *Cucumis melo* (Fang et al., 86th Annual Meeting of the American Society for Horticultural Science *Hort Science* (1989) 24: 89);

grape, *Vitis vinifera* (Colby et al., Symposium on Plant Gene Transfer, UCLA Symposia on Molecular and Cellular Biology *J Cell Biochem Suppl* (1989) 13D: 255 mango, *Mangifera indica* (Mathews, et al., symposium on Plant Gene Transfer, UCLA Symposia on Molecular and Cellular Biology *J Cell Biochem Suppl* (1989) 13D :264);

and for the following monocots:

rice, *Oryza sativa* (Shimamoto et al., *Nature* (1989) 338: 274);

rye, *Secale cereale* (de la Pena et al., *Nature* (1987) 325: 274);

maize, (Rhodes et al., *Science* (1988) 240: 204).

In addition regeneration of whole plants from cells (not necessarily transformed) has been observed in apricot, *Prunus armeniaca* (Pieterse, *Plant Cell Tissue and Organ Culture* (1989) 19: 175);

asparagus, *Asparagus officinalis* (Elmer et al., *J Amer Soc Hort Sci* (1989) 114: 1019);

banana, hybrid Musa (Escalant and Teisson, *Plant Cell Reports* (1989) 7: 665);

bean, *Phaseolus vulgaris* (McClean and Grafton, *Plant Science* (1989) 60: 117);

cherry, hybrid Prunus (Ochatt et al., *Plant Cell Reports* (1988) 7: 393);

grape, *Vitis vinifera* (Matsuta and Hirabayashi, *Plant Cell Reports* (1989) 7: 684);

mango, *Mangifera indica* (DeWald et al., *J Amer Soc Hort Sci* (1989) 114: 712);

melon, *Cucumis melo* (Moreno et al., *Plant Sci letters* (1985) 34: 195);

ochra, *Abelmoschus esculentus* (Roy and Mangat, *Plant Science* (1989) 60: 77; Dirks and van Buggenum, *Plant Cell Reports* (1989) 7: 626);

onion, hybrid *Allium* (Lu et al., *Plant Cell Reports* (1989) 7: 696);

orange, *Citrus sinensis* (Hidaka and Kajikura, *Scientia Horiculturae* (1988) 34: 85);

papaya, *Carrica papaya* (Litz and Conover, *Plant Sci Letters* (1982) 26: 153);

peach, *Prunus persica* and plum, *Prunus domestica* (Mante et al., *Plant Cell Tissue and Organ Culture* (1989) 19: 1);

pear, *Pyrus communis* (Chevreau et al., *Plant Cell Reports* (1988) 2: 688; Ochatt and Power, *Plant Cell Reports* (1989) 7: 587);

pineapple, *Ananas comosus* (DeWald et al., *Plant Cell Reports* (1988) 7: 535);

watermelon, *Citrullus vulgaris* (Srivastava et al., *Plant Cell Reports* (1989) 8: 300);

wheat, *Triticum aestivum* (Redway et al., *Plant Cell Reports* (1990) 8: 714).

The regenerated plants are transferred to standard soil conditions and cultivated in a conventional manner.

Although the following plant cells have been genetically transformed with foreign DNA, the indicated reports do not describe regeneration:

grape, *Vitus vinifera* (Baribault et al., *Plant Cell Reports* (1989) 8: 137);

orange, *Citrus sinensis* (Kobayashi and Uchimiya, *Japan J Genet* (1989) 64: 91);

papaya, *Carica papaya* (Pang and Sanford, *J Amer Soc Hort Sci* (1989) 113: 287);

pea, *Pisum sativum* (Puonti-Kaerlas et al., Plant Cell Reports(1989) 8: 321);

peach, *Prunus persica* (Hammerschlag et al., *J Amer Soc Hort Sci* (1989) 114: 508);

sugarbeet, *Beta vulgaris* (Lindsey and Jones, *Plant Cell Reports* (1989) 8: 71).

After the expression cassette is stably incorporated into regenerated transgenic plants, it can be transferred to other plants by sexual crossing. Any of a number of standard breeding techniques can be used, depending upon the species to be crossed.

The plants are grown and harvested using conventional procedures, and the desired edible portions recovered. In some instances, the edible portions are directly consumed as in the case of, for example, fruits such as tomato, peach, pear, etc. This may also be true of vegetative parts such as carrots, celery, and potato; or of edible seeds, such as peanuts, pecans, or sunflower seeds. If the edible portion is to be used in prepared foodstuffs, the recipe for preparation may conveniently be altered to reduce the sweetening component which would otherwise be added. For example, endogenously sweetened pumpkin used to make pumpkin pudding or pie filling, endogenously sweetened apples used in applesauce or apple pie, and endogenously sweetened rice used in making rice pudding would be employed in recipes of reduced sugar content, as illustrated in Example 6 below. Depending on the lability to heat exhibited by the particular embodiment of monellin or thaumatin chosen, adjustments of amounts may need to be made in accordance with the cooking steps in the preparation procedure. Other modifications and adjustments of recipes employing these endogenously sweetened edible parts will be apparent and readily made by practitioners of the culinary art.

Thus, the expression cassette providing for constitutive or specialized-organ production of thaumatin or monellin, contained in a suitable vector, is transformed into plant cells or explants, which are then regenerated into stably transformed transgenic plants with edible parts having endogenously enhanced sweetness. These plants are then cultivated conventionally to yield edible portions with increased sweetness.

EXAMPLES

The following examples are intended to illustrate the invention but not to limit its scope.

Example 1

Preparation of a Synthetic Monellin Gene

A single chain protein of the amino acid sequence obtained by direct fusion of the B and A chains of FIG. 1 is encoded by a synthetic DNA sequence constructed as follows. In the synthetic gene, nucleotides 1–141 encode residues 1–46 of the native B chain preceded by a met encoding ATG start codon, nucleotides 142–165 encode the linking "C" portion of 8 amino acids representing residues 47–50 of the native B chain and residues 2–5 of the native A chain, and nucleotides 166–285 encode residues 6–45 of the native A protein. The complete construct is shown in FIG. 4. In summary, the construct encodes amino acid residues 1–46 of the native B subunit, residues 6–45 of the native A subunit, and a "C" linker of the sequence Tyr-Glu-Asn-Glu-Arg-Glu-Ile-Lys (SEQ ID NO:19).

This synthetic gene was prepared from the following oligomers, synthesized using Applied Biosystems 380B DNA Synthesizer.

```
5'-->3'
U1: TATGGGAGAATGGGAAATTATCGATATTGGACCATTCACTCAAAAC    (SEQ ID NO:20) (46mer)
U2: TTGGGTAAGTTCGCTGTTGACGAAGAAAACAAGATTGGTCAATAT    (SEQ ID NO:21) (45mer)
U3: GGTAGATTGACTTTCAACAAGGTTATTAGACCATGTATGAAGAAG    (SEQ ID NO:22) (45mer)
U4: ACTATTTACGAAAACGAAAGAGAAATTAAGGGGTACGAATACCAA    (SEQ ID NO:23) (45mer)
U5: TTGTATGTTTACGCTTCTGACAAGCTTTTCAGAGCTGACATTTCT    (SEQ ID NO:24) (45mer)
U6: GAAGACTACAAGACCCGCGGTAGAAAGTTGTTGAGATTCAACGGT    (SEQ ID NO:25) (45mer)
U7: CCAGTTCCACCACCATAATAG                            (SEQ ID NO:26) (21mer)
L1: CGATAATTTCCCATTCTCCCA                            (SEQ ID NO:27) (21mer)
L2: CGTCAACAGCGAACTTACCCAAGTTTTGAGTGAATGGTCCAATAT    (SEQ ID NO:28) (45mer)
L3: CCTTGTTGAAAGTCAATCTACCATATTGACCAATCTTGTTTTCTT    (SEQ ID NO:29) (45mer)
L4: CTCTTTCGTTTTCGTAAATAGTCTTCTTCATACATGGTCTAATAA    (SEQ ID NO:30) (45mer)
L5: TGTCAGAAGCGTAAACATACAATTGGTATTCGTACCCCTTAATTT    (SEQ ID NO:31) (45mer)
L6: TACCGCGGGTCTTGTAGTCTTCAGAAATGTCAGCTCTGAAAAGCT    (SEQ ID NO:32) (45mer)
L7: TCGACTATTATGGTGGTGGAACTGGACCGTTGAATCTCAACAACTTTC (SEQ ID NO:33) (48mer)
```

The oligomers were isolated by urea-polyacrylamide gel electrophoresis and purified by passing through a Sep-pak C18 column (Whatman) and annealed and ligated as shown:

```
NdeI                                              SalI
   U1    U2    U3    U4    U5    U6    U7
   ─── ─── ─── ─── ─── ─── ───
     ─── ─── ─── ─── ─── ─── ───
   L1    L2    L3    L4    L5    L6    L7
``` to obtain the synthetic gene of FIG. 3 bracketed by NdeI or NcoI at the 5' end and SalI at the 3' end. One such example is shown in FIG. 4.

For the ligation, each oligomer was phosphorylated at 37° C. for 45 minutes in a reaction mixture of 30 μl containing 50 mM Tris-HCl, pH 8.0, 10 mM $MgCl_2$, 10 mM DTT, 1 mMATP, and 5 units of T4 polynucleotide kinase. Each reaction mixture was pooled, extracted by phenol/chloroform, precipitated with ethanol, and dried under Speed-Vac. The dried pellet was dissolved in 50 μl distilled water and 7 μl ligation buffer (0.2M Tris-HCl, pH 7.5, 0.1M MgCl$_2$, 0.1M DTT) added. The solution was placed in a 95° C. water-bath and cooled slowly to room temperature overnight. To the mixture was added 7 μl of 10 mM ATP, 40 units of T4 DNA ligase (New England Biolab Inc.) and 2 μl of water.

The reaction mixture was kept at room temperature for 10 minutes, extracted by phenol/chloroform, precipitated, dried and redissolved in 85 μl water. The ligated oligomer mixture was treated with restriction endonuclease NdeI and SalI (New England Biolabs, Inc.), and the 290 base pair fragment was isolated by electrophoresis with a 7% polyacrylamide gel, the band electroeluted and purified using the Elutip-D column (S&S Co.).

M13mp19RF was used for cloning the synthetic monellin gene. M13mp19RF was cut with XbaI/SalI (New England Biolabs, Inc.), and the large fragment was isolated and purified. A synthetic XbaI/NdeI adaptor,

```
     XbaI                                              NdeI
5'- CTAGAAACTGCAATGTTGAATAAACGCTGATTTTCGATCA  - 3' (40mer) (SEQ ID NO:34)
3'-     TTTGACGTTACAACTTATTTGCGACTAAAAGCTAGTAT  - 5' (38mer) (SEQ ID NO:35)
``` was purified, and the NdeI/SalI digested, annealed synthetic monellin DNA fragment prepared above was combined with XbaI/SalI-treated M13mp19RF and XbaI/NdeI adaptor in 10 μl of 20 mM Tris-HCl, pH 7.5, 10 mM MgCl$_2$, 10 mM DTT, 200 units T4 DNA ligase (New England Biolabs, Inc.) and incubated at 4° C. overnight to provide M13mp19 MON-1RF. The ligation mixture was transformed into hosts by adding 5 μl of the ligation mixture to 200 μl of *E. coli* JM101 competent cells (Messing, J., *Methods in Enzymology* (1983) 101: 20–78), and the desired sequence was confirmed by dideoxy sequencing (Sanger, T., et al., *Proc Natl Acad Sci* USA (1985) 74: 5463–5467).

Example 2

Construction of E8/Monellin Expression System

The 2.0 kb fragment containing the E8 promoter was isolated from pE8mutRN2.0 (Giovannoni et al., *The Plant Cell* (1989) 1:53) by cleaving with NcoI. The 5' overhang of the NcoI site was filled in with the large fragment of DNA polymerase (Klenow fragment) and the linearized plasmid was digested with EcoRI. The resulting 2.0 kb EcoRI/filled NcoI fragment was ligated into pUC118 which had been cleaved with EcoRI and SmaI. The resulting construction, pE8mutRN2.0(+), retains the original NcoI site and includes BamHI, XbaI, SalI, PstI, SphI, and HindIII sites respectively, downstream of the NcoI site.

The NcoI-SalI fused monellin gene of Example 1 was ligated into pE8mutRN2.0(+) cleaved with NcoI and SalI. Ligated plasmids were then transformed into *E. coli* HB101, and plasmid DNA was isolated from the resulting clones. Cleaving with NcoI and SalI demonstrated that an insert of the proper size was generated. The resulting 2.3 kb E8-monellin insert in pUC118 was liberated by digestion with EcoRI and SalI followed by agarose gel purification.

The 2.3 kb E8-monellin fragment (EcoRI-SalI) was combined in a 3-way ligation with the 0.25 kb SalI/EcoRI Agrobacterium nopaline synthase gene transcription terminator fragment purified from pUCnos-ter, and with EcoRI cleaved pUC118. (pUCnos-ter was generated by subcloning the 0.25 kb SstI/EcoRI nopaline synthase gene transcription termination sequence from pBI121 (Clonetech Inc., Palo Alto, Calif.) into pUC118 digested with EcoRI and SstI.) Restriction enzyme digestion and dideoxy sequencing analysis of miniprep DNA isolated from resulting clones demonstrated that the resulting vector, pE8mon, contained the E8 5' regulatory sequences ligated precisely at the ATG start of translation to the fused monellin gene, whose 3' SalI site was ligated to the SalI site of the nopaline synthase transcription termination fragment.

The 2.55 kb insert of pE8-mon was liberated with EcoRI and ligated into the intermediate co-integrative plant transformation vector pMLJ1 (similar to those described by De Block et al., *EMBO J* (1984) 2: 1681–1689) in both orientations to generate pMLJ1:E8-monellin(D) and pMLJ1:E8-monellin(I). In pMLJ1:E8-monellin(D), the 5'-end of the E8-monellin-terminator insert is closest to the bacterial ampicillin resistance locus; in pMLJ1:E8-monellin(I), the nopaline synthase terminator sequences are closest to this locus.

Example 3

Construction of CaMV-monellin Expression System

A 0.8 kb EcoRI/SmaI CaMV 35S promoter fragment was prepared by adding an EcoRI linker to the 5' end of the regulatory sequences of the cauliflower mosaic virus 35S promoter isolated from pBI121 (Clonetech Inc., Palo Alto, Calif.). This fragment was purified by agarose gel electrophoresis.

pE8mon (Example 2) was cleaved with NcoI and the NcoI 5' overhang was filled in with DNA polymerase (Klenow) to generate a blunt end suitable for ligation with the SmaI site of the purified CaMV 35S promoter described above, and the resulting linearized plasmid was digested with EcoRI. The 0.55 kb blunt/EcoRI monellin-terminator fragment was isolated by agarose gel electrophoresis and employed in a tri-molecular ligation with the 0.8 kb EcoRI/SmaI CaMV 35S promoter, and with pUC119 cleaved with EcoRI, to generate pCaMV-monellin. Mapping of restriction endonuclease sites demonstrated that pCaMV-monellin consists of pUC118 in which the EcoRI site harbors an insert consisting of the CaMV 35S promoter ligated at the 3' SmaI site to the blunt-ended 5' NcoI site of the fused monellin gene, whose 3' end in turn is ligated at the SalI site to the nopaline synthase transcription termination sequence.

The 1.35 kb insert of pCaMV-monellin was liberated by EcoRI and purified from an agarose gel. The resulting 1.35 kb fragment was ligated into the EcoRI site of pMLJ1 in both orientations. In pMLJ1:CaMV-monellin(D), the CaMV 35S regulatory sequences of the CaMV 35S promoter-monellin-terminator construction are closest to the ampicillin resistance locus of pMLJ1; in pMLJ1:CaMV-monellin (I), the nopaline synthase gene transcription termination sequences are closest to this locus.

Example 4

Co-integration of Monellin Gene Vectors

Triparental mating (Van Haute et al., *EMBO J* (1983) 2: 411–417) of *E. coli* MV1193 harboring pMLJ1:E8-monellin (D), pMLJ1:E8-monellin(I), pCaMV-monellin(D), or pMLJ1:CaMV-monellin(I) with *Agrobacterium tumefaciens* containing the cointegrative plant transformation vector pGV3850 (Zambryski et al., *EMBO J* (1983) 2: 2143–2150) and the helper *E. coli* strain pGJ23 (Van Haute et al., (1983) supra), resulted in cointegration of the constructions into pGV3850. The resulting vectors pGV3850:E8-monellin(D), pGV3850:E8-monellin(I), pGV3850:CaMV-monellin(D), and pGV3850:CaMV-monellin(I) were then utilized to insert chimeric fused monellin genes into the genomes of both tomato and lettuce.

Example 5

Transformation of Tomato and Lettuce with Fused Monellin Gene Constructions

Sterile cotyledon pieces of tomato or lettuce were infected with Agrobacterium containing the cointegrated plasmids of Example 4 which are Ti plasmids which include, within the transferred T-DNA, a neomycin phosphotransferase gene (NPTII) capable of conferring kanamycin resistance in transgenic plants. The co-integrative *Agrobacterium tumefaciens* Ti vector, pGV3850, with the plasmid pMLJ1:E8-monellin(D), pMLJ1:E8-monellin(I), pMLJ1:CaMV-monellin(D), or pMLJ1:CaMV-monellin(I) integrated into it, prepared as described in Example 4, was employed to facilitate DNA transfer of the fused monellin gene constructions into independent tomato genomes, while only the CaMV-containing versions of these vector constructions, also described in Example 4, were inserted into independent lettuce genomes. The procedure is as follows:

To prepare the host plants for transformation, seeds of tomato or lettuce were germinated as described to form cotyledons. The cotyledons were then transferred to feeder plates and cocultivated with the bacteria and then placed on regeneration medium. After shoots were formed, the shoots and dark green callus were transferred to shooting medium to stimulate further production of shoots. Shoots were then transferred to rooting medium to stimulate root formation. The plants were then transferred to soil and potted.

Preparation of Feeder Plates

Feeder plates were prepared using thick petri plates of approximately 40 ml of Xanthi culture medium with 8 g/l agar and inoculated with 1 ml of a thick Xanthi suspension culture (7 days old).

Xanthi medium contains

|  |  | (stock) |
| --- | --- | --- |
| 1 bottle KC MS Salts (MM100) | 4.3 g |  |
| i-inositol | 100 mg |  |
| sucrose | 30 g |  |
| $KH_2PO_4$ | 2 ml | 100 mg/ml |
| thiamine | 1.3 ml | 1 mg/ml |
| 2,4-D | 2 ml | 100 mg/l |
| kinetin | 0.4 ml | 0.25 mg/ml | and is prepared by adjusting the pH to 5.5 with KOH and diluting with $H_2O$ to 1 liter. 100 ml aliquots are placed into 500 ml flasks and flasks plugged and capped with aluminum foil; the medium is then autoclaved for 20 minutes.

The tobacco Xanthi suspension culture was then filtered through a 40 mesh filter once per week, and 10 ml of filtrate were added to 100 ml of Xanthi medium in a 500 ml flask.

The plates were sealed with parafilm and incubated for 12 hours in the growth chamber (25° C.) on a lighted shelf.

Generation of Cotyledons

Tomato and lettuce seeds were sterilized in a flow-hood by stirring for no more than two minutes in 20 ml 70% EtOH using approximately 50 seeds in a 50 ml beaker at a time to loosen the gelatinous seed coat. The seeds were rinsed once with sterile distilled water and stirred 5 minutes in 20% Purex bleach mixed with 2 drops of Tween 80 (Sigma), and then rinsed 4 times with sterile distilled water.

Using sterile forceps, 12 to 15 seeds were placed on each petri plate, containing Germination Medium, which was then wrapped with parafilm and then with aluminum foil. These plates were prepared as follows:

"Tomato Germination Medium" prepared from 1 pkg MS Medium mixed with KC MM-100 and 3% sucrose (30 g sucrose in 800 ml $H_2O$). The medium is finished by adjusting the pH to 5.7 with KOH, adjusting the volume to 1 liter; and then adding 8 g bacto agar (0.8% agar). The medium is autoclaved 20 minutes and poured into thick petri plates (about 30 ml per plate).

The seeds were allowed to grow at 25° C.; after 5 days (when the seeds had reached about 60% germination), they were removed from the aluminum foil and grown under 2500 lux, with a 16 hour photoperiod. The seedlings were grown for a total of 8 days.

"Lettuce germination medium" was prepared from 1% agar containing half-strength Hoagland's solution (Hewitt, E. J. (1966) *Sand and Water Culture Methods*, Commonwealth Ag. Bureau) and 10 µg/ml gibberellic acid (Sigma catalog number G-3250). The medium was autoclaved 20 minutes and poured into thick petri plates (30 ml per plate).

The seeds were allowed to grow at 25° C. under 2500 lux with a 16 hour photoperiod for four days.

CoCultivation on Feeder Plates

Tomato (*Lycopersicon esculentum* cultivars Ailsa Craig and Castlemart) and lettuce (*Lactuca sativa*, cultivar Dark Green Boston Mont.) cotyledon pieces were cocultivated with the bacteria for 48 hours on tobacco feeder plates. The feeder cells increase the efficiency of transformation.

The cotyledons germinated as described above were placed on the feeder plates, as follows. Cotyledons were cut with a scalpel in a drop of $H_2O$ in a petri plate. The scalpel was rocked gently to make the cuts thus minimizing tearing and bruising of the tissue. Only the ends of the cotyledons were cut off.

Cut cotyledons were placed cuticle side down onto sterile Whatman #1 filter paper which had been placed on the feeder plate. Approximately 50 cotyledon pieces were placed on each plate. The plates were sealed with parafilm and placed in the growth chamber for 16 hours.

The cotyledons were infected using cultures of the Agrobacterium containing pMLJ1:E8-monellin(D), pMLJ1:E8-monellin(I), pMLJ1:CaMV-monellin(D) and pMLJ1:CaMV-monellin(I) which had been grown overnight in 10 ml YEB medium supplemented with 25 µg/ml spectinomycin, and diluted four-fold in Germination Medium (described above) to an $OD_{590}$ of 0.5. 5 ml of diluted bacteria was aliquoted into a petri dish followed by addition of 30 cotyledon pieces previously co-cultivated with the tobacco feeder cells. The Agrobacterium/cotyledon mixture was swirled to wet for 5 minutes.

The cotyledons were touched once to a sterile paper towel, and placed back on the same feeder plates cuticle side down and co-cultivated for an additional 48 hours.

After co-cultivation with the bacteria, tomato cotyledons were placed on "Regeneration Medium" cuticle side up. The edges curl down into the agar ensuring the wounded surfaces will be in direct contact with drugs. 15 cotyledon pieces were placed on each plate. From this stage on, antibiotics were used to inhibit the growth of Agrobacterium (Cefotaxime) and to select for transformed plant cells (kanamycin).

"Tomato regeneration medium" contains in 1 liter:

4.3 g MS Salts (KC MM-100)

30 g glucose 0.59 g MES 2 ml 500X Gamborgs vitamins[1]

pH to 5.8 with 1N KOH volume to 1 liter 8 g tissue culture grade agar

Autoclave 20 minutes

Cool to 50° C.

Add: 1 mg sterile zeatin (trans-isomer) 300 mg/l cefotaxime (Calbiochem Cat# 219380) 50 mg/l kanamycin (Cefotaxime is light sensitive; plates containing Cefotaxime were made the day before use.)

[1]500X Gamborgs vitamins: 5 g myo-inositol 0.5 g thiamine HCL 50 mg nicotinic acid 50 mg pyridoxine HCl 100 ml sterile water After co-cultivation with the bacteria, lettuce cotyledons were placed on "callus medium" with the cuticle side up.

"Lettuce Callus Medium" contains in 1 liter: 4.3 gm MS salts (KC MM-100) 30 g sucrose 2 ml 500 X Gamborg's Vitamins pH to 5.8 with 1N KOH volume to 1 liter 8 gm tissue culture grade agar Autoclave 20 minutes Cool to 50° C.

Add: 0.5 mg sterile kinetin 0.1 mg indole-3-acetic acid (Sigma I-1250) 300 mg cefotaxime (Calbiochem 219380) 50 mg kanamycin After 12 (5 days in the dark and 7 days in the light with a 16 hour photoperiod), the lettuce cotyledons were transferred from the lettuce callus medium to the lettuce regeneration medium.

"Lettuce Regeneration Medium" contains in 1 liter:

4.3 gm MS salts (KC MM-100)

30 g sucrose 2 ml 500 X Gamborg's Vitamins pH to 5.8 with 1N KOH adjust volume to 1 liter 8 gm tissue culture grade agar Autoclave 20 minutes Cool to 50° C.

Add: 0.05 mg kinetin 0.05 mg zeatin 300 mg cefotaxime 50 mg kanamycin

Shooting and Rooting Procedures

For both tomato and lettuce, within 10 days callus was visible at the edges of the infected and regenerating cotyledons. Cotyledon pieces were transferred to fresh plates every 2 weeks. Shoots and dark green callus were transferred to Shooting Medium (same as Regeneration Medium except that the zeatin concentration is reduced to 0.1 mg/ml). After 6 weeks (3 transfers) all callus and shoots had been transferred to Shooting Medium.

The tomato plantlets were then rooted as follows: TM5 rooting medium, described by Shahin, E. A., *Theor Appl Gen* (1985) 69: 235–240 was used but the levels of kanamycin and cefatoxime were reduced to 25 mg/l and 125 mg/l, respectively, for use in the rooting procedure. TM5 for root induction contains

| | amount/liter |
|---|---|
| MS Salts | 4.3 g |
| Potato vitamins (200X)[2] | 5 ml |
| Sucrose | 30 g |
| IBA (indole-3-butyric acid, Sigma) | 0.1 mg (add before autoclaving) |
| Purified agar | 7 g. |

To complete the medium; pH was adjusted to 5.8 with KOH, and the medium autoclaved 15 minutes. When cooled to 50° C. 25 mg kanamycin and 125 mg cefotaxime were added.

[2]Potato vitamins (200X) myo-inositol 20 g thiamine-HCl 100 mg pyridoxine-HCl 100 mg nicotinic acid 1 g glycine 500 mg biotin 10 mg folic acid 100 mg Petri plates with the above-described TM5 rooting medium were prepared. The tomato shoots prepared adjust pH to 5.8 to 6.0 to clear solution. Store at −20° C. as described above were excised and placed upright in the rooting medium. Roots were observed after 2–4 weeks.

In exactly the same manner, shoots obtained from the lettuce transformants are rooted.

Transplantation

Rooted tomato plants were transferred to soil by removing them gently from the agar using a spatula to scrape away most of the agar. The roots were rinsed in warm water to remove as much agar as possible. The roots were then planted in clay pots and these were placed inside GA-7 boxes. The covers of the boxes were opened over several days, and watered with ½-strength Hoagland's solution every other watering. After 2 weeks completely uncovered in the growth chamber the plants were transplanted into large pots and moved to the greenhouse. In the exact same manner rooted lettuce plants are transplanted.

The resulting transgenic tomatoes and lettuce have enhanced sweet taste due to the integrated monellin gene. For those tomato plants transformed with the monellin gene under control of the E8 promoter, only the tomato fruit shows enhanced sweetness. For the lettuce and the tomato plants transformed with monellin under the control of the CaMV promoter, all portions of the plant have an enhanced sweet taste.

In a manner entirely similar to that set forth above for obtaining lettuce and tomatoes endogenously sweetened with monellin, lettuce and tomato endogenously sweetened with thaumatin can also be obtained.

Example 6

Use of the Sweetened Edible Plants in Preparation of Food

The following illustrates the alteration possible in preparation procedures for foodstuffs using the transgenic plants of the invention or their edible parts.

A. Preparation of stewed tomatoes:

1. Standard recipe.

2 cups tomatoes, cut up 1 tbsp sugar bay leaf salt and pepper to taste

2. Recipe using endogenously sweetened tomatoes.

2 cups tomatoes, cut up bay leaf salt and pepper to taste

Salad dressing.

1. For salads containing natural lettuce.

½ cup olive oil
¼ cup garlic vinegar
¼ cup red wine
2 tsp sugar
salt and pepper to taste
2. For salads containing sweetened lettuce.
½ cup olive oil
¼ cup garlic vinegar
¼ cup red wine
salt and pepper to taste As illustrated above, the sweetening of prepared foodstuffs using sugar or other carbohydrate sweetening agents can be reduced by the inclusion of the endogenously sweetened foodstuffs of the invention.

---

We claim:

1. A recombinant expression system capable, when inserted into a higher plant, of expressing the gene encoding a single-chain monellin, which system comprises a nucleotide sequence encoding said single-chain monellin operably linked to control sequences effective in said higher plant,
   wherein said single-chain monellin is of the formula B-C-A;
   wherein B represents a peptide portion at least 90% homologous to residues 1-46 of the B chain of native monellin depicted in SEQ ID NO:2 and modified only by conservative substitutions;
   C is a covalent bond or a peptide portion of 1-10 gene-encoded amino acids; and
   A represents a peptide portion at least 90% homologous to residues 6-45 of the A chain of native monellin depicted in SEQ ID NO: 1 and modified only by conservative substitution.

2. The expression system of claim 1 wherein said control sequences include a promoter organ-specific to ripening fruit.

3. The expression system of claim 2 wherein said promoter is organ specific to fruit which exhibits ethylene-controlled ripening.

4. The expression system of claim 3 wherein said promoter is the tomato E8 promoter.

5. The expression system of claim 1 wherein said control sequences include a constitutive promoter.

6. The expression system of claim 5 wherein said promoter is the cauliflower mosaic virus 35S promoter.

7. The expression system of claim 1 wherein said control sequences include a promoter which is a seed storage protein promoter.

8. The expression system of claim 1 wherein said control sequences include a promoter which is a vegetable-specific promoter.

9. Plant cells transformed with the expression system of claim 1.

10. Plant cells of claim 9 wherein said cells are cells of a higher plant which produces edible fruit.

11. The plant cells of claim 10 which are selected from the group consisting of apple, apricot, banana, blackberry, cherry, red raspberry, tomato, melon, grape, mango, orange, lemon, lime, grapefruit, papaya, peach, pear, pineapple, plum, strawberry, and watermelon.

12. The plant cells of claim 9 wherein said higher plant produces edible vegetable parts.

13. The plant cells of claim 12 which are selected from asparagus, carrot, celery, onion, potato, lettuce, cabbage, cauliflower, cucumber, and sugar beet.

14. The plant cells of claim 9 wherein said higher plant produces edible seeds.

15. The plant cells of claim 14 which are selected from pecan, peanut, walnut, rice, corn, wheat, rye, soybean, bean, pea, and sunflower.

16. A transgenic plant which produces edible fruit, seed or vegetable, wherein said transgenic property is conferred by the presence of the expression system of claim 1.

17. The transgenic plant of claim 16 which produces edible fruits.

18. The transgenic plant of claim 16 which produces edible seeds.

19. The transgenic plant of claim 16 which produces edible vegetable parts.

20. An edible fruit, seed or vegetable which contains the expression system of claim 1.

21. An edible fruit, seed or vegetable produced by a transgenic plant containing the expression system of claim 1.

22. A method to prepare edible fruit, seed or vegetable which comprises cultivating the plants of claim 16, and recovering the edible fruit, seed or vegetable.

23. The expression system of claim 1 wherein the B protein portion sequence is

| (Met) | Gly | Glu | Trp | Glu | Ile | Ile | Asp | Ile | Gly |
|---|---|---|---|---|---|---|---|---|---|
| Pro | Phe | Thr | Gln | Asn | Leu | Gly | Lys | Phe | Ala |
| Val | Asp | Glu | Glu | Asn | Lys | Ile | Gly | Gln | Tyr |
| Gly | Arg | Leu | Thr | Phe | Asn | Lys | Val | Ile | Arg |
| Pro | Cys | Met | Lys | Lys | Thr | Ile (residues of 1-46 of SEQ ID NO: 2). | | | |

24. The expression system of claim 1 wherein the A protein portion is

| | | | | | Gly | Tyr | Glu | Tyr | Gln |
|---|---|---|---|---|---|---|---|---|---|
| Leu | Tyr | Val | Tyr | Ala | Ser | Asp | Lys | Leu | Phe |
| Arg | Ala | Asp | Ile | Ser | Glu | Asp | Tyr | Lys | Thr |
| Arg | Gly | Arg | Lys | Leu | Leu | Arg | Phe | Asn | Gly |
| Pro | Val | Pro | Pro | Pro (residues 6-45 of SEQ ID NO: 1). | | | | | |

25. The expression system of claim 1 wherein C is a covalent bond or has the formula

A1-A2-A3-A4-A5-A6-A7-A8-A9-A10 wherein each of A1-A3 represents an amino acid residue and each of A4-A10 represents an amino acid residue or is not present, and wherein a majority of the amino acid residues are hydrophilic.

26. The expression system of claim 25 wherein A2, A4 and A6 are acidic amino acids; A5 and A8 are basic amino acids; A3 is a polar neutral amino acid; and A1 and A7 are nonpolar amino acids, and A9 and A10 are absent.

27. The expression system of claim 26 wherein C has the formula selected from the group consisting of Tyr—Glu—Asn—Glu—Arg—Glu—Ile—Lys (SEQ ID NO:7);
Tyr—Ala—Ser—Asp—Lys (SEQ ID NO:14);
Glu—Asp—Tyr—Lys—Thr—Arg (residues 1-6 of SEQ ID NO:17);
Tyr—Glu—Asn—Arg—Glu—Asp—Ile—Lys (SEQ ID NO:8);
Tyr—Lys—Thr—Arg—Glu—Asp—Ile—Lys (SEQ ID NO:9);
Tyr—Glu—Arg—Glu—Ile—Lys (SEQ ID NO:10);
Tyr—Glu—Asn—Ile—Lys (SEQ ID NO:11);
Tyr—Glu—Ile—Lys (SEQ ID NO:12);
Tyr—Tyr—Ala—Ser—Asp—Lys—Leu—Lys (SEQ ID NO:13);
Tyr—Ala—Ser—Asp—Lys—Leu (SEQ ID NO:15);
Tyr—Ser—Asp—Lys (SEQ ID NO:16);
Glu—Asp—Tyr—Lys—Thr—Arg—Gly—Arg (SEQ ID NO:17); and
Glu—Asp—Tyr—Thr—Arg (SEQ ID NO:18).

28. The expression system of claim 27 wherein C has the formula Tyr-Glu-Asn-Glu-Arg-Glu-Ile-Lys (SEQ ID NO:7).

29. The plant cells of claim 7 wherein said expression system encodes a single chain monellin wherein the B protein portion sequence is:

| (Met) | Gly | Glu | Trp | Glu | Ile | Ile | Asp | Ile | Gly |
|-------|-----|-----|-----|-----|-----|-----|-----|-----|-----|
| Pro   | Phe | Thr | Gln | Asn | Leu | Gly | Lys | Phe | Ala |
| Val   | Asp | Glu | Glu | Asn | Lys | Ile | Gly | Gln | Tyr |
| Gly   | Arg | Leu | Thr | Phe | Asn | Lys | Val | Ile | Arg |
| Pro   | Cys | Met | Lys | Lys | Thr | Ile (residues 1–46 of SEQ ID NO: 2); | | | |

C has the formula Tyr-Glu-Asn-Glu-Arg-Glu-Ile-Lys (SEQ ID NO:7); and the A protein portion is

|     |     |     |     |     | Gly | Tyr | Glu | Tyr | Gln |
|-----|-----|-----|-----|-----|-----|-----|-----|-----|-----|
| Leu | Tyr | Val | Tyr | Ala | Ser | Asp | Lys | Leu | Phe |
| Arg | Ala | Asp | Ile | Ser | Glu | Asp | Tyr | Lys | Thr |
| Arg | Gly | Arg | Lys | Leu | Leu | Arg | Phe | Asn | Gly |
| Pro | Val | Pro | Pro | Pro (residues 6–45 of SEQ ID NO: 1). | | | | | |

30. The transgenic plant of claim 14 wherein the expression system encodes a single chain monellin wherein the B protein portion sequence is

| (Met) | Gly | Glu | Trp | Glu | Ile | Ile | Asp | Ile | Gly |
|-------|-----|-----|-----|-----|-----|-----|-----|-----|-----|
| Pro   | Phe | Thr | Gln | Asn | Leu | Gly | Lys | Phe | Ala |
| Val   | Asp | Glu | Glu | Asn | Lys | Ile | Gly | Gln | Tyr |
| Gly   | Arg | Leu | Thr | Phe | Asn | Lys | Val | Ile | Arg |
| Pro   | Cys | Met | Lys | Lys | Thr | Ile (residues 6–45 of SEQ ID NO: 1); | | | |

C has the formula Tyr-Glu-Asn-Glu-Arg-Glu-Ile-Lyz (SEQ D NO:7); and
the A protein portion is

|     |     |     |     |     | Gly | Tyr | Glu | Tyr | Gln |
|-----|-----|-----|-----|-----|-----|-----|-----|-----|-----|
| Leu | Tyr | Val | Tyr | Ala | Ser | Asp | Lys | Leu | Phe |
| Arg | Ala | Asp | Ile | Ser | Glu | Asp | Tyr | Lys | Thr |
| Arg | Gly | Arg | Lys | Leu | Leu | Arg | Phe | Asn | Gly |
| Pro | Val | Pro | Pro | Pro (residues 6–45 of SEQ ID NO: 1). | | | | | |

31. The fruit, seed or vegetable of claim 17 wherein said expression system encodes a single chain monellin wherein the B protein portion sequence is

| (Met) | Gly | Glu | Trp | Glu | Ile | Ile | Asp | Ile | Gly |
|-------|-----|-----|-----|-----|-----|-----|-----|-----|-----|
| Pro   | Phe | Thr | Gln | Asn | Leu | Gly | Lys | Phe | Ala |
| Val   | Asp | Glu | Glu | Asn | Lys | Ile | Gly | Gln | Tyr |
| Gly   | Arg | Leu | Thr | Phe | Asn | Lys | Val | Ile | Arg |
| Pro   | Cys | Met | Lys | Lys | Thr | Ile (residues 1–46 of SEQ ID NO: 2); | | | |

C has the formula Tyr-Glu-Asn-Glu-Arg-Glu-Ile-Lys (SEQ ID NO:7); and
the A protein portion is

|     |     |     |     |     | Gly | Tyr | Glu | Tyr | Gln |
|-----|-----|-----|-----|-----|-----|-----|-----|-----|-----|
| Leu | Tyr | Val | Tyr | Ala | Ser | Asp | Lys | Leu | Phe |
| Arg | Ala | Asp | Ile | Ser | Glu | Asp | Tyr | Lys | Thr |
| Arg | Gly | Arg | Lys | Leu | Leu | Arg | Phe | Asn | Gly |
| Pro | Val | Pro | Pro | Pro (residues 6–45 of SEQ ID NO: 1). | | | | | |

32. A method to prepare edible fruit, seed or vegetable which comprises cultivating the plants of claim 30 and recovering the edible fruit, seed or vegetable.

* * * * *

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Phe  Arg  Glu  Ile  Lys  Gly  Tyr  Glu  Tyr  Gln  Leu  Tyr  Val  Tyr  Ala  Ser
1                   5                        10                       15

Asp  Lys  Leu  Phe  Arg  Ala  Asp  Ile  Ser  Glu  Asp  Tyr  Lys  Thr  Arg  Gly
               20                        25                       30

Arg  Lys  Leu  Leu  Arg  Phe  Asn  Gly  Pro  Val  Pro  Pro  Pro
               35                        40                       45
```

( 2 ) INFORMATION FOR SEQ ID NO:2:

( i ) SEQUENCE CHARACTERISTICS:
        ( A ) LENGTH: 50 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Gly  Glu  Trp  Glu  Ile  Ile  Asp  Ile  Gly  Pro  Phe  Thr  Gln  Asn  Leu  Gly
1                   5                        10                       15

Lys  Phe  Ala  Val  Asp  Glu  Glu  Asn  Lys  Ile  Gly  Gln  Tyr  Gly  Arg  Leu
               20                        25                       30

Thr  Phe  Asn  Lys  Val  Ile  Arg  Pro  Cys  Met  Lys  Lys  Thr  Ile  Tyr  Glu
               35                        40                       45

Asn  Glu
     50
```

( 2 ) INFORMATION FOR SEQ ID NO:3:

( i ) SEQUENCE CHARACTERISTICS:
        ( A ) LENGTH: 285 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..285

( x i ) SEQUENCE DESCRIPTION: SEQ ID NO:3:

```
ATG  GGA  GAA  TGG  GAA  ATT  ATC  GAT  ATT  GGA  CCA  TTC  ACT  CAA  AAC  TTG     48
Met  Gly  Glu  Trp  Glu  Ile  Ile  Asp  Ile  Gly  Pro  Phe  Thr  Gln  Asn  Leu
1                   5                        10                       15

GGT  AAG  TTC  GCT  GTT  GAC  GAA  GAA  AAC  AAG  ATT  GGT  CAA  TAT  GGT  AGA     96
```

|  |  |  |  |  |  |  |  |  |  |  |  |  |  |  |  |
|---|---|---|---|---|---|---|---|---|---|---|---|---|---|---|---|
| Gly | Lys | Phe | Ala<br>20 | Val | Asp | Glu | Glu | Asn<br>25 | Lys | Ile | Gly | Gln | Tyr<br>30 | Gly | Arg |

| TTG | ACT | TTC | AAC | AAG | GTT | ATT | AGA | CCA | TGT | ATG | AAG | AAG | ACT | ATT | TAC | 144 |
|---|---|---|---|---|---|---|---|---|---|---|---|---|---|---|---|---|
| Leu | Thr | Phe<br>35 | Asn | Lys | Val | Ile | Arg<br>40 | Pro | Cys | Met | Lys | Lys<br>45 | Thr | Ile | Tyr | |

| GAA | AAC | GAA | AGA | GAA | ATT | AAG | GGG | TAC | GAA | TAC | CAA | TTG | TAT | GTT | TAC | 192 |
|---|---|---|---|---|---|---|---|---|---|---|---|---|---|---|---|---|
| Glu | Asn<br>50 | Glu | Arg | Glu | Ile | Lys<br>55 | Gly | Tyr | Glu | Tyr | Gln<br>60 | Leu | Tyr | Val | Tyr | |

| GCT | TCT | GAC | AAG | CTT | TTC | AGA | GCT | GAC | ATT | TCT | GAA | GAC | TAC | AAG | ACC | 240 |
|---|---|---|---|---|---|---|---|---|---|---|---|---|---|---|---|---|
| Ala<br>65 | Ser | Asp | Lys | Leu | Phe<br>70 | Arg | Ala | Asp | Ile | Ser<br>75 | Glu | Asp | Tyr | Lys | Thr<br>80 | |

| CGC | GGT | AGA | AAG | TTG | TTG | AGA | TTC | AAC | GGT | CCA | GTT | CCA | CCA | CCA | | 285 |
|---|---|---|---|---|---|---|---|---|---|---|---|---|---|---|---|---|
| Arg | Gly | Arg | Lys | Leu<br>85 | Leu | Arg | Phe | Asn | Gly<br>90 | Pro | Val | Pro | Pro | Pro<br>95 | | |

( 2 ) INFORMATION FOR SEQ ID NO:4:

( i ) SEQUENCE CHARACTERISTICS:
        ( A ) LENGTH: 95 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met<br>1 | Gly | Glu | Trp | Glu<br>5 | Ile | Ile | Asp | Ile | Gly<br>10 | Pro | Phe | Thr | Gln | Asn<br>15 | Leu |
|---|---|---|---|---|---|---|---|---|---|---|---|---|---|---|---|
| Gly | Lys | Phe | Ala<br>20 | Val | Asp | Glu | Glu | Asn<br>25 | Lys | Ile | Gly | Gln | Tyr<br>30 | Gly | Arg |
| Leu | Thr | Phe<br>35 | Asn | Lys | Val | Ile | Arg<br>40 | Pro | Cys | Met | Lys | Lys<br>45 | Thr | Ile | Tyr |
| Glu | Asn<br>50 | Glu | Arg | Glu | Ile | Lys<br>55 | Gly | Tyr | Glu | Tyr | Gln<br>60 | Leu | Tyr | Val | Tyr |
| Ala<br>65 | Ser | Asp | Lys | Leu | Phe<br>70 | Arg | Ala | Asp | Ile | Ser<br>75 | Glu | Asp | Tyr | Lys | Thr<br>80 |
| Arg | Gly | Arg | Lys | Leu<br>85 | Leu | Arg | Phe | Asn | Gly<br>90 | Pro | Val | Pro | Pro | Pro<br>95 | |

( 2 ) INFORMATION FOR SEQ ID NO:5:

( i ) SEQUENCE CHARACTERISTICS:
        ( A ) LENGTH: 292 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

| CATGGGAGAA | TGGGAAATTA | TCGATATTGG | ACCATTCACT | CAAAACTTGG | GTAAGTTCGC | 60 |
|---|---|---|---|---|---|---|
| TGTTGACGAA | GAAAACAAGA | TTGGTCAATA | TGGTAGATTG | ACTTTCAACA | AGGTTATTAG | 120 |
| ACCATGTATG | AAGAAGACTA | TTTACGAAAA | CGAAAGAGAA | ATTAAGGGGT | ACGAATACCA | 180 |
| ATTGTATGTT | TACGCTTCTG | ACAAGCTTTT | CAGAGCTGAC | ATTTCTGAAG | ACTACAAGAC | 240 |
| CCGCGGTAGA | AAGTTGTTGA | GATTCAACGG | TCCAGTTCCA | CCACCATAAT | AG | 292 |

( 2 ) INFORMATION FOR SEQ ID NO:6:

( i ) SEQUENCE CHARACTERISTICS:
        ( A ) LENGTH: 292 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

-continued

```
TCGACTATTA TGGTGGTGGA ACTGGACCGT TGAATCTCAA CAACTTTCTA CCGCGGGTCT    60

TGTAGTCTTC AGAAATGTCA GCTCTGAAAA GCTTGTCAGA AGCGTAAACA TACAATTGGT   120

ATTCGTACCC CTTAATTTCT CTTTCGTTTT CGTAAATAGT CTTCTTCATA CATGGTCTAA   180

TAACCTTGTT GAAAGTCAAT CTACCATATT GACCAATCTT GTTTCTTCG TCAACAGCGA    240

ACTTACCCAA GTTTTGAGTG AATGGTCCAA TATCGATAAT TTCCCATTCT CC           292
```

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

Tyr Glu Asn Glu Arg Glu Ile Lys
    1                5

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

Tyr Glu Asn Arg Glu Asp Ile Lys
    1                5

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

Tyr Lys Thr Arg Glu Asp Ile Lys
    1                5

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:10:

Tyr Glu Arg Glu Ile Lys
    1                5

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:11:

Tyr Glu Asn Ile Lys
    1                5

( 2 ) INFORMATION FOR SEQ ID NO:12:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

Tyr  Glu  Ile  Lys
  1

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:13:

Tyr  Tyr  Ala  Ser  Asp  Lys  Leu  Lys
  1                            5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:14:

Tyr  Ala  Ser  Asp  Lys
  1                     5

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:15:

Tyr  Ala  Ser  Asp  Lys  Leu
  1                     5

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:16:

Tyr  Ser  Asp  Lys
  1

( 2 ) INFORMATION FOR SEQ ID NO:17:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:17:

Glu Asp Tyr Lys Thr Arg Gly Arg
1               5

( 2 ) INFORMATION FOR SEQ ID NO:18:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( x i ) SEQUENCE DESCRIPTION: SEQ ID NO:18:

Glu Asp Tyr Thr Arg
1               5

( 2 ) INFORMATION FOR SEQ ID NO:19:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:19:

Tyr Glu Asn Glu Arg Glu Ile Lys
1               5

( 2 ) INFORMATION FOR SEQ ID NO:20:

( i ) SEQUENCE CHARACTERISTICS:
      ( A ) LENGTH: 46 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:20:

TATGGGAGAA TGGGAAATTA TCGATATTGG ACCATTCACT CAAAAC      46

( 2 ) INFORMATION FOR SEQ ID NO:21:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:21:

TTGGGTAAGT TCGCTGTTGA CGAAGAAAAC AAGATTGGTC AATAT      45

( 2 ) INFORMATION FOR SEQ ID NO:22:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:22:

GGTAGATTGA CTTTCAACAA GGTTATTAGA CCATGTATGA AGAAG      45

( 2 ) INFORMATION FOR SEQ ID NO:23:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:23:

ACTATTTACG AAAACGAAAG AGAAATTAAG GGGTACGAAT ACCAA    45

( 2 ) INFORMATION FOR SEQ ID NO:24:

( i ) SEQUENCE CHARACTERISTICS:
  ( A ) LENGTH: 45 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:24:

TTGTATGTTT ACGCTTCTGA CAAGCTTTTC AGAGCTGACA TTTCT    45

( 2 ) INFORMATION FOR SEQ ID NO:25:

( i ) SEQUENCE CHARACTERISTICS:
  ( A ) LENGTH: 45 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:25:

GAAGACTACA AGACCCGCGG TAGAAAGTTG TTGAGATTCA ACGGT    45

( 2 ) INFORMATION FOR SEQ ID NO:26:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:26:

CCAGTTCCAC CACCATAATA G    21

( 2 ) INFORMATION FOR SEQ ID NO:27:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:27:

CGATAATTTC CCATTCTCCC A    21

( 2 ) INFORMATION FOR SEQ ID NO:28:

( i ) SEQUENCE CHARACTERISTICS:
  ( A ) LENGTH: 45 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:28:

CGTCAACAGC GAACTTACCC AAGTTTTGAG TGAATGGTCC AATAT    45

( 2 ) INFORMATION FOR SEQ ID NO:29:

( i ) SEQUENCE CHARACTERISTICS:
  ( A ) LENGTH: 45 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:29:

CCTTGTTGAA AGTCAATCTA CCATATTGAC CAATCTTGTT TTCTT    45

( 2 ) INFORMATION FOR SEQ ID NO:30:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

CTCTTTCGTT TTCGTAAATA GTCTTCTTCA TACATGGTCT AATAA    45

( 2 ) INFORMATION FOR SEQ ID NO:31:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

TGTCAGAAGC GTAAACATAC AATTGGTATT CGTACCCCTT AATTT    45

( 2 ) INFORMATION FOR SEQ ID NO:32:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

TACCGCGGGT CTTGTAGTCT TCAGAAATGT CAGCTCTGAA AAGCT    45

( 2 ) INFORMATION FOR SEQ ID NO:33:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

TCGACTATTA TGGTGGTGGA ACTGGACCGT TGAATCTCAA CAACTTTC    48

( 2 ) INFORMATION FOR SEQ ID NO:34:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

CTAGAAACTG CAATGTTGAA TAAACGCTGA TTTTCGATCA    40

( 2 ) INFORMATION FOR SEQ ID NO:35:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear (xi) SEQUENCE DESCRIPTION: SEQ ID NO:35:

TATGATCGAA AATCAGCGTT TATTCAACAT TGCAGTTT    38